US012800454B2

(12) United States Patent
He et al.

(10) Patent No.: US 12,800,454 B2
(45) Date of Patent: Nov. 17, 2026

(54) SAMPLE BOX LOADING AND UNLOADING STORAGE TROLLEY OF ROCK TRUE-TRIAXIAL TEST INSTRUMENT

(71) Applicant: Northeastern University, Shenyang City (CN)

(72) Inventors: Benguo He, Shenyang City (CN); Hongyuan Fu, Shenyang City (CN); Xiating Feng, Shenyang City (CN); Hongpu Li, Shenyang City (CN); Jie Wang, Shenyang City (CN); Hanyi Liu, Shenyang City (CN)

(73) Assignee: Northeastern University, Shenyang City (CN)

( * ) Notice: Subject to any disclaimer, the term of this patent is extended or adjusted under 35 U.S.C. 154(b) by 308 days.

(21) Appl. No.: 18/713,546

(22) PCT Filed: Sep. 11, 2023

(86) PCT No.: PCT/CN2023/117901
§ 371 (c)(1),
(2) Date: May 24, 2024

(87) PCT Pub. No.: WO2025/043753
PCT Pub. Date: Mar. 6, 2025

(65) Prior Publication Data

US 2026/0168899 A1 Jun. 18, 2026

(30) Foreign Application Priority Data

Aug. 28, 2023 (CN) ........................ 202311086017.9

(51) Int. Cl.
*B62B 3/04* (2006.01)
*B62B 5/04* (2006.01)
(Continued)

(52) U.S. Cl.
CPC ............... *G01N 3/02* (2013.01); *G01N 33/24* (2013.01); *G01N 2001/002* (2013.01);
(Continued)

(58) Field of Classification Search
CPC .... G01N 3/02; G01N 33/24; G01N 2001/002; G01N 2203/0206; G01N 2203/0256;
(Continued)

(56) References Cited

U.S. PATENT DOCUMENTS 3,817,169 A * 6/1974 Bischoff ................ B30B 9/321 221/268
5,058,911 A * 10/1991 Hunter ..................... B25H 1/12 212/196
5,619,246 A * 4/1997 Straayer ............... H04N 1/0635 347/262
2004/0086367 A1 * 5/2004 Isaacs ....................... B62B 3/04 414/679

(Continued)

FOREIGN PATENT DOCUMENTS

CN 105823695 A * 8/2016 ............... G01N 3/02
CN 105842054 A * 8/2016 ............ G01N 3/317

(Continued)

*Primary Examiner* — Jaimin G Patel
(74) *Attorney, Agent, or Firm* — MUNCY, GEISSLER, OLDS & LOWE, P.C.

(57) ABSTRACT

Provided is a sample box loading and unloading storage trolley of a rock true-triaxial test instrument. The trolley includes a trolley support framework fixed on a lower trolley platform, at four corner positions of a bottom of which trolley moving wheels and trolley support legs are arranged. A distribution box and an operation station are arranged on the lower trolley platform. A trolley connecting plate is arranged above the trolley support framework and slidably connected to an upper trolley platform through a transverse electric moving device, the upper trolley platform is slidably connected to a lifting device support plate through a longitudinal electric moving device, and electric push rods are fixed at four corners of an upper part of the lifting device support plate; and sample box grippers are arranged above the electric push rods, and a fixing plate is arranged above the sample box grippers.

7 Claims, 5 Drawing Sheets

(51) Int. Cl.
*G01N 3/02* (2006.01)
*G01N 33/24* (2006.01)
*G01N 1/00* (2006.01)

(52) U.S. Cl.
CPC ................ *G01N 2203/0206* (2013.01); *G01N 2203/0256* (2013.01); *G01N 2203/0447* (2013.01)

(58) Field of Classification Search
CPC .... G01N 2203/0447; B62B 3/02; B62B 3/04; B62B 3/10; B62B 5/04
See application file for complete search history.

(56) References Cited

U.S. PATENT DOCUMENTS

| | | | | |
|---|---|---|---|---|
| 2006/0160684 | A1* | 7/2006 | Springston | B30B 15/028 483/1 |
| 2017/0214817 | A1* | 7/2017 | Nie | H04N 1/40056 |

FOREIGN PATENT DOCUMENTS

| | | | | | |
|---|---|---|---|---|---|
| CN | 205657357 | U | | 10/2016 | |
| CN | 205801170 | U | * | 12/2016 | |
| CN | 208094044 | U | | 11/2018 | |
| CN | 209520832 | U | | 10/2019 | |
| CN | 110562775 | A | * | 12/2019 | B65G 35/00 |
| CN | 209783871 | U | | 12/2019 | |
| CN | 111807024 | A | * | 10/2020 | B65G 47/56 |
| CN | 112319586 | A | * | 2/2021 | B62B 3/04 |
| CN | 113344139 | A | * | 9/2021 | G06N 3/045 |
| CN | 113715886 | A | * | 11/2021 | B62B 3/02 |
| KR | 20140115578 | A | | 10/2014 | |

* cited by examiner

SAMPLE BOX LOADING AND UNLOADING STORAGE TROLLEY OF ROCK TRUE-TRIAXIAL TEST INSTRUMENT

BACKGROUND OF THE INVENTION

1. Field of the Invention

The present invention relates to the technical field of rock true triaxial tests, in particular to a sample box loading and unloading storage trolley of a rock true-triaxial test instrument.

2. The Prior Arts

Rock burst is one of major disasters faced by deep underground engineering, and the issue of the rock burst is receiving increasing attention from researchers. Domestic and foreign scholars have conducted a large number of deep hard rock experiments and developed deep hard rock experimental equipment.

With development and progress of a rock true-triaxial experiment technology, various types of equipment and instruments emerge one after another. Among the prior art, true-triaxial equipment, due to its special loading method, has more complex steps of mounting samples, often requiring manual carrying and mounting, or using mechanical equipment such as overhead cranes to assist in mounting. However, true-triaxial instrument and equipment require high material stiffness, and the equipment is relatively heavy, whereby accuracy is difficult to control by methods of manual carrying or overhead cranes etc., and high accuracy of lifting positions of sample boxes cannot be achieved, greatly reducing experiment efficiency. In addition, most of the overhead cranes are laboratory public equipment, and on-demand use is difficult to ensure. Moreover, the overhead cranes are difficult to operate, and easy to swing, equipment collisions are easy to cause, and in severe cases, experiment personnel may be accidentally harmed, posing significant safety hazards.

Therefore, in response to the above problems, the present invention proposes a sample box loading and unloading storage trolley of a rock true-triaxial test instrument. Grippers can be replaced for different equipment, on-demand use can be achieved, the sample box loading and unloading storage trolley is more convenient to use, experiment efficiency is greatly improved, precise rigid lifting of the sample boxes is achieved, the accuracy of the lifting positions of the sample boxes is greatly improved, shaking in the loading and unloading process with the overhead cranes is eliminated, equipment damage or injury to experiment personnel caused by shaking of the sample boxes is avoided, and the safety of the experiment is improved.

SUMMARY OF THE INVENTION

In response to existing problems, the present invention provides a sample box loading and unloading storage trolley of a rock true-triaxial test instrument. The sample box loading and unloading storage trolley includes a trolley support framework, wherein the trolley support framework is fixed on a lower trolley platform, and a lower weight box is arranged in the trolley support framework; trolley moving wheels and trolley support legs are arranged at four corner positions of a bottom of the lower trolley platform, a trolley handrail is fixed at a front end of the lower trolley platform, and a distribution box and an operation console are arranged on the lower trolley platform between the trolley handrail and the trolley support framework; a trolley connecting plate is arranged above the trolley support framework, an upper part of the trolley connecting plate is slidably connected to an upper trolley platform through a transverse electric moving device, an upper part of the upper trolley platform is slidably connected to a lifting device support plate through a longitudinal electric moving device, electric push rods are fixed at four corners of an upper part of the lifting device support plate, an upper weight box is arranged on the lifting device support plate, and the upper weight box is located in a space surrounded by the electric push rods; and sample box grippers are arranged above the electric push rods, and a fixing plate is arranged above the sample box grippers.

Sliding rails in a transverse arrangement are symmetrically arranged on an upper surface of the trolley connecting plate, two pairs of sliding blocks are symmetrically arranged on the sliding rails, besides, the sliding blocks are at a lower end of the upper trolley platform, and a length of the sliding rails is the same as a transverse length of the trolley connecting plate; and a longitudinal length of the trolley connecting plate is the same as that of the upper trolley platform, and the transverse length of the trolley connecting plate is smaller than or equal to that of the upper trolley platform.

Guide rails in a longitudinal arrangement are symmetrically arranged on an upper surface of the upper trolley platform, two pairs of sliding blocks are symmetrically arranged on the guide rails, the sliding blocks are at a lower end of the lifting device support plate, a transverse width of the upper trolley platform is the same as that of the lifting device support plate, and a longitudinal length of the upper trolley platform is larger than that of the lifting device support plate.

The transverse electric moving device and the longitudinal electric moving device have a same structure, and each include a moving motor, a speed reducer, a ball screw and a fixing block.

The moving motor of the transverse electric moving device is arranged at an outermost end of the trolley connecting plate, the moving motor is connected to the speed reducer, the speed reducer is fixed at a position of a protruding block at a longitudinal edge of the trolley connecting plate, the ball screw is connected to an output end of the speed reducer, a length of the ball screw is smaller than or equal to a transverse length of the trolley connecting plate; the fixing block sleeves the ball screw, and the fixing block is fixed at a bottom of the upper trolley platform.

The moving motor of the longitudinal electric moving device is arranged at an outermost end of the upper trolley platform, the moving motor is connected to the speed reducer, the speed reducer is fixed at a transverse edge of the upper trolley platform, the ball screw is connected to an output end of the speed reducer, a length of the ball screw is smaller than or equal to a longitudinal length of the upper trolley platform, the fixing block sleeves the ball screw, and the fixing block is fixed at a bottom of the lifting device support plate.

The trolley moving wheels include two universal wheels and two one-way wheels, the universal wheels are mounted at a bottom of the lower trolley platform on a side of the trolley handrail, and the one-way wheels are mounted at the bottom of the lower trolley platform away from the side of the trolley handrail.

The trolley support legs include electric lifting rods and support legs, lower ends of the electric lifting rods are connected to the support legs, and upper ends of the electric lifting rods are connected to the lower trolley platform.

The sample box grippers include grappling fixtures and stable connecting plates, the grappling fixtures and the stable connecting plates are an integral structure, and clamping blocks being 0.5 cm in height are arranged at front ends of the grappling fixtures.

The sample box loading and unloading storage trolley of the present invention has the following beneficial effects.

Compared with traditional hoisting equipments, the sample box loading and unloading storage trolley of a rock true-triaxial test instrument is simple in structure and low in cost, and the trolley is convenient to move; besides, the sample box grippers can be replaced for different equipment, whereby loading and unloading requirements of different equipment are met; and precise rigid lifting can be realized, a problem of mutual collisions between the equipments generated by shaking in a loading and unloading process with the overhead cranes is avoided, a contact area between the lifting equipment and the sample boxes is enlarged, safety hazards generated in a process of loading and unloading the sample boxes with the overhead cranes are avoided, and it is ensured that tests are performed safely and efficiently.

In drawings: 1: trolley handrail; 2: lower trolley platform; 3: trolley moving wheel; 4: trolley support leg; 4*a*: electric lifting rod; 4*b*: support leg; 5: distribution box; 6: operation console; 7: lower weight box 8: trolley support framework; 9: trolley connecting plate; 10: longitudinal electric moving device; 11: upper trolley platform; 12: transverse electric moving device 13: lifting device support plate; 14: electric push rod; 15: guide rail; 16: upper weight box; 17: sample box gripper; 17*a*: grappling fixture; 17*b*: stable connecting plate; 18: fixing plate; 19: sample box; 20: clamping block; 21: sliding rail; 22: sliding block; 191: falling guiding block; 201: moving motor; 202: speed reducer; 203: ball screw; 204: fixing block.

DETAILED DESCRIPTION OF THE PREFERRED EMBODIMENT

The present invention will be further described in detail in combination with accompanying drawings and specific examples.

Figure 1:
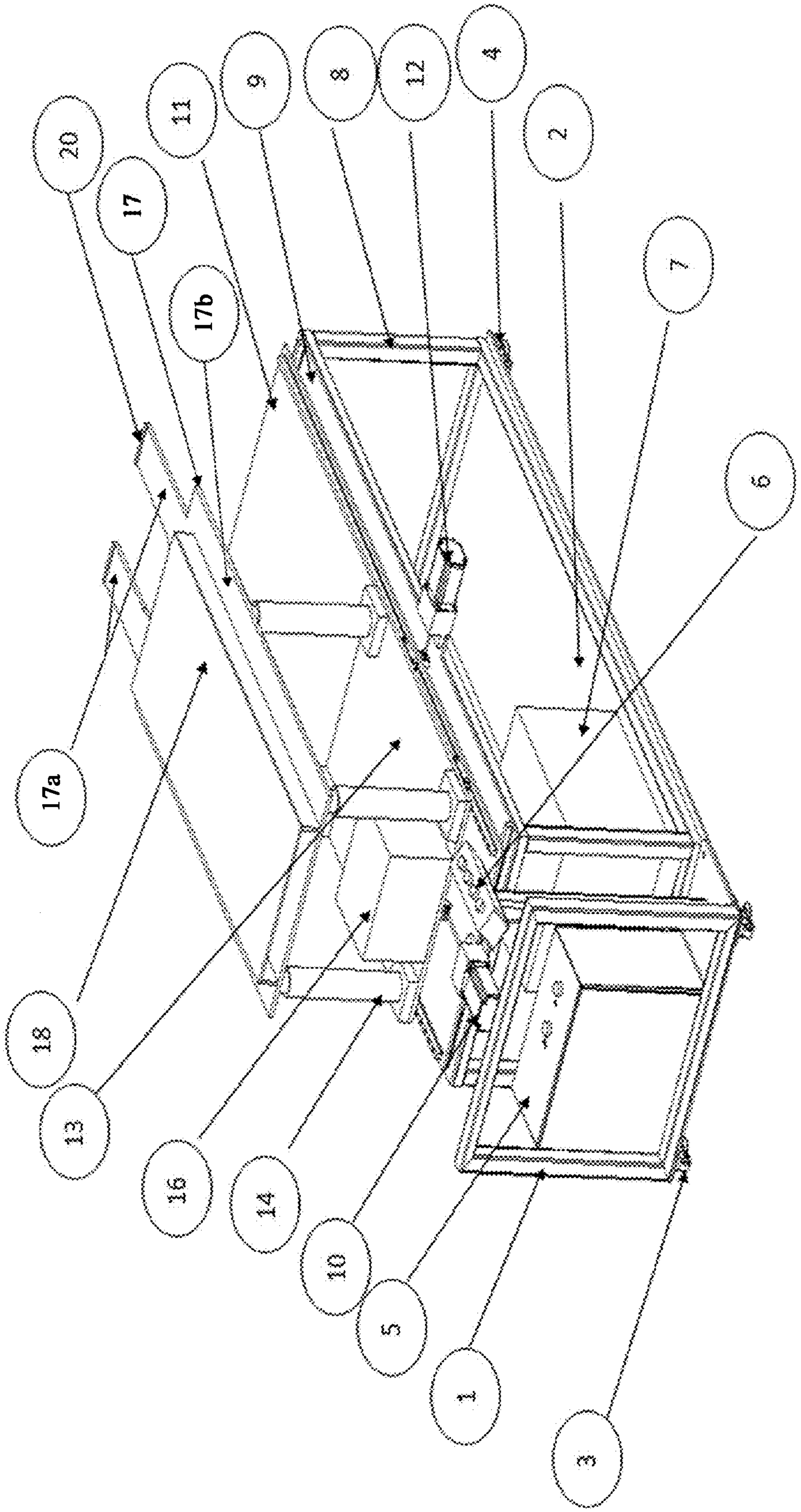
FIG. 1 shows a schematic structural view of a sample box loading and unloading storage trolley of a rock true-triaxial test instrument of the present invention.
Figure 2:
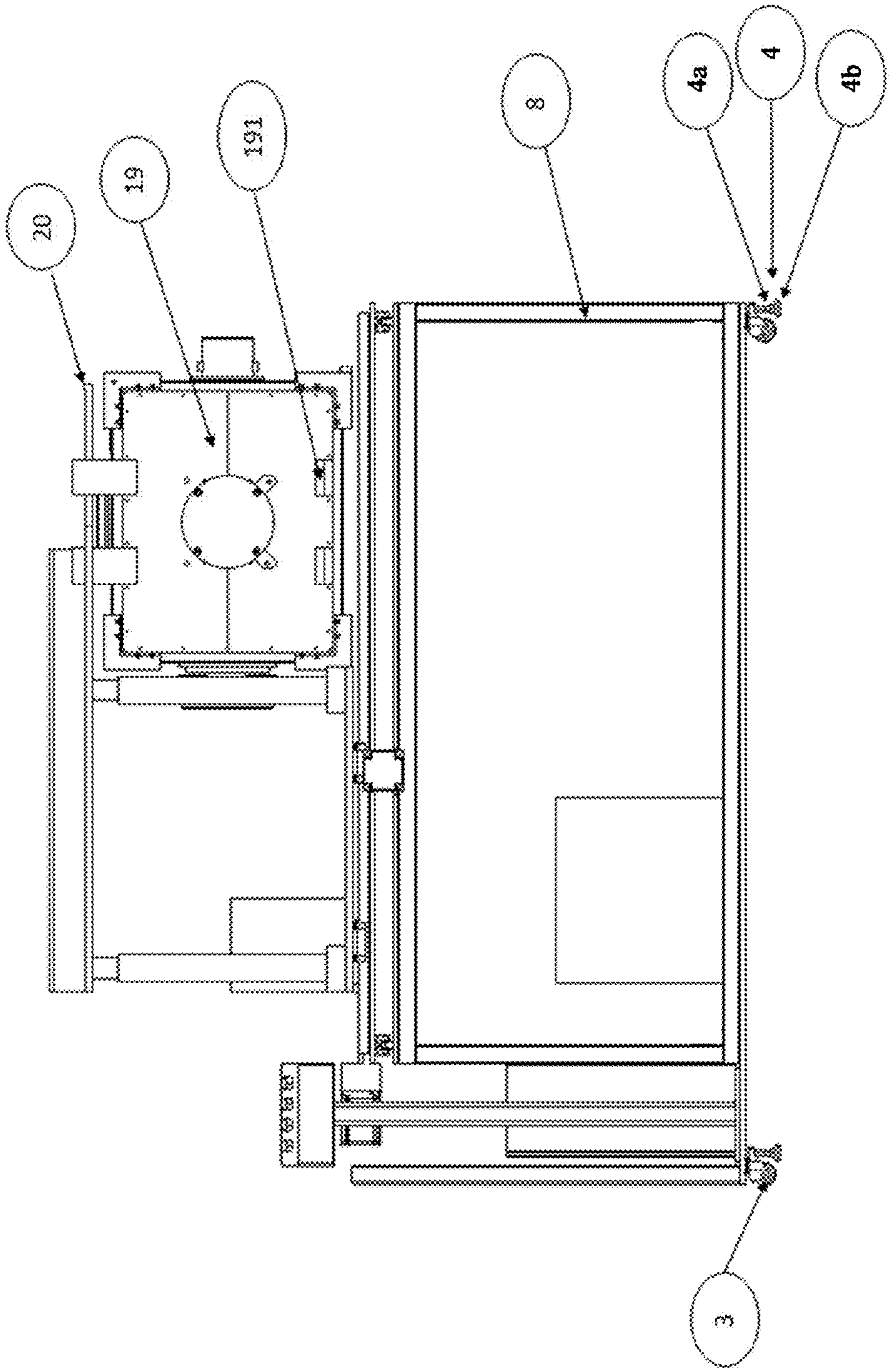
FIG. 2 shows a side view of positions of the sample box loading and unloading storage trolley of the rock true-triaxial test instrument and a sample box during operations.
Figure 3:
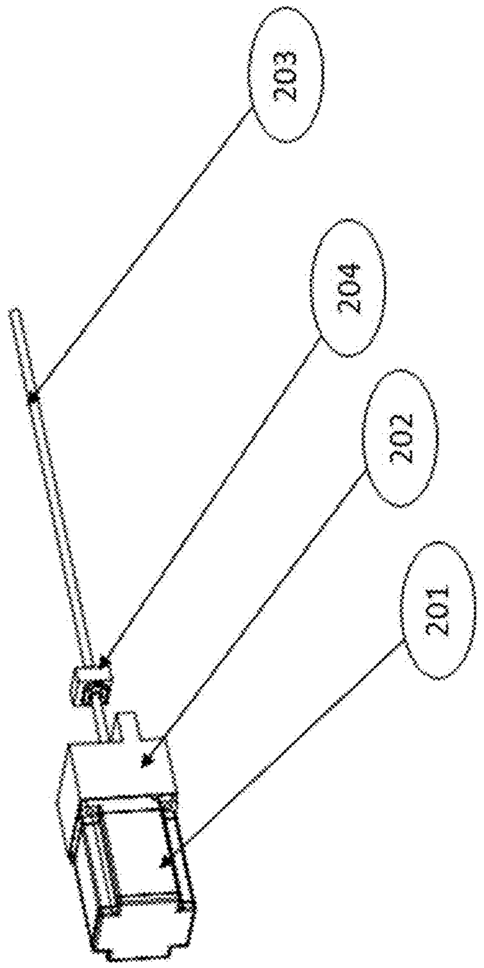
FIG. 3 shows a structural diagram of a transverse electric moving device of the sample box loading and unloading storage trolley of the rock true-triaxial test instrument of the present invention.
Figure 4:
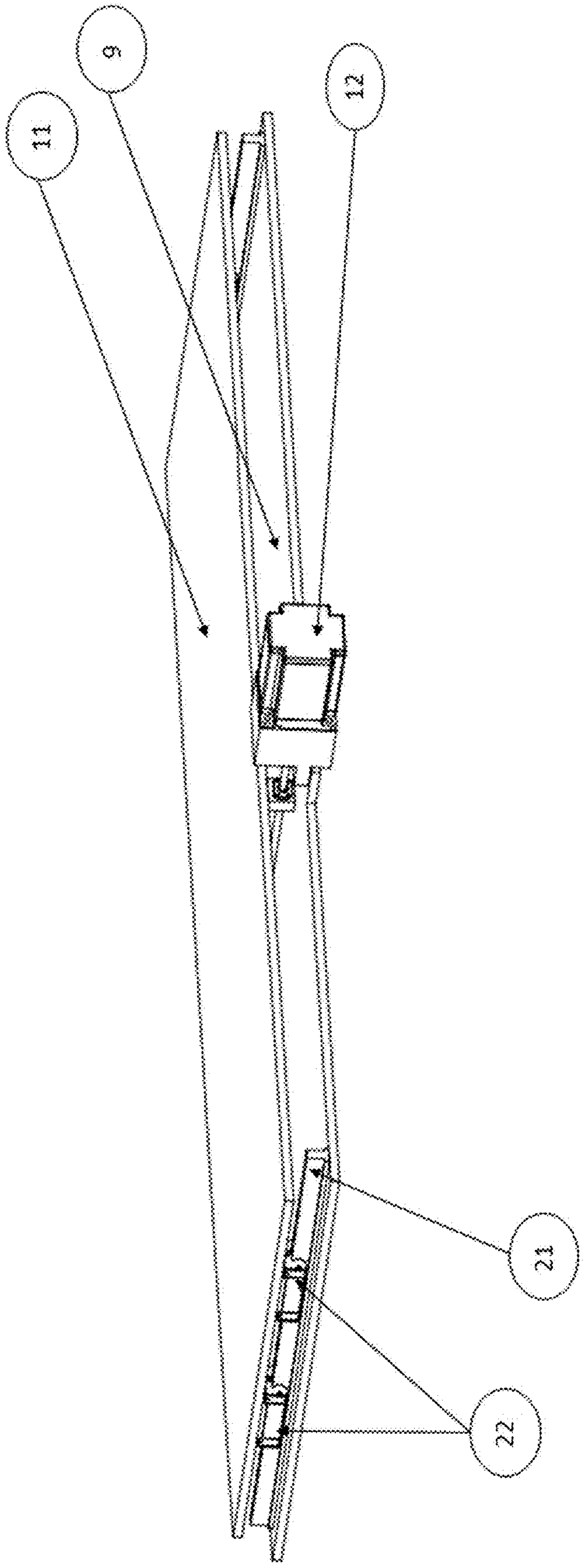
FIG. 4 shows a position relationship view of the transverse electric moving device of the sample box loading and unloading storage trolley of the rock true-triaxial test instrument of the present invention.
Figure 5:
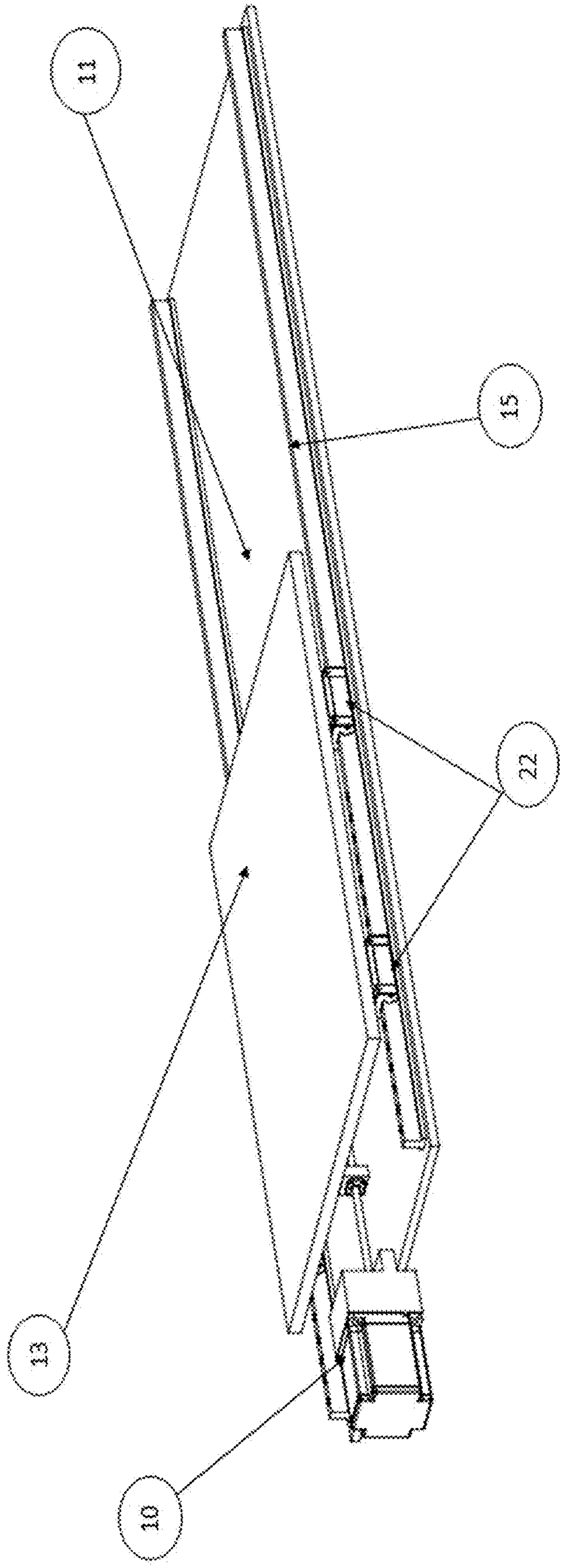
FIG. 5 shows a position relationship view of a longitudinal electric moving device of the sample box loading and unloading storage trolley of the rock true-triaxial test instrument of the present invention.

As shown in FIGS. 1-5, a sample box loading and unloading storage trolley of a rock true-triaxial test instrument includes a trolley support framework 8, wherein the trolley support framework 8 is fixed on a lower trolley platform 2, and a lower weight box 7 is arranged in the trolley support framework 8; trolley moving wheels 3 and trolley support legs 4 are arranged at four corner positions of a bottom of the lower trolley platform 2, a trolley handrail 1 is fixed at a front end of the lower trolley platform 2, and a distribution box 5 and an operation console 6 are arranged on the lower trolley platform 2 between the trolley handrail 1 and the trolley support framework 8; a trolley connecting plate 9 is arranged above the trolley support framework 8, an upper part of the trolley connecting plate 9 is slidably connected to an upper trolley platform 11 through a transverse electric moving device 12, an upper part of the upper trolley platform 11 is slidably connected to a lifting device support plate 13 through a longitudinal electric moving device 10, electric push rods 14 are fixed at four corners of an upper part of the lifting device support plate 13, an upper weight box 16 is arranged on the lifting device support plate 13, and the upper weight box 16 is located in a space surrounded by the electric push rods 14; and sample box grippers 17 are arranged above the electric push rods 14, a fixing plate 18 is arranged above the sample box grippers 17, and the fixing plate 18 can increase lifting stability of the electric push rods 14 and ensure synchronous lifting of all the electric push rods 14. For different sample boxes 19, the fixing plate 18 can be disassembled, and the sample box grippers 17 can be replaced, whereby operation requirements of other sample boxes are met.

Sliding rails 21 in a transverse arrangement are symmetrically arranged on an upper surface of the trolley connecting plate 9, two pairs of sliding blocks 22 are symmetrically arranged on the sliding rails 21, besides, the sliding blocks 22 are at a lower end of the upper trolley platform 11, and a length of the sliding rails 21 is the same as a transverse length of the trolley connecting plate 9; and a longitudinal length of the trolley connecting plate 9 is the same as that of the upper trolley platform 11, and the transverse length of the trolley connecting plate 9 is smaller than or equal to that of the upper trolley platform 11.

Guide rails 15 in a longitudinal arrangement are symmetrically arranged on an upper surface of the upper trolley platform 11, two pairs of sliding blocks 22 are symmetrically arranged on the guide rails 15, besides, the sliding blocks 22 are at a lower end of the lifting device support plate 13, a transverse width of the upper trolley platform 11 is the same as that of the lifting device support plate 13, and a longitudinal length of the upper trolley platform 11 is larger than that of the lifting device support plate 13.

The transverse electric moving device 12 and the longitudinal electric moving device 10 have a same structure, and each include a moving motor 201, a speed reducer 202, a ball screw 203 and a fixing block 204; and the longitudinal electric moving device 10 and the transverse electric moving device 12 can adjust a moving speed to accurately control rising and falling positions of the sample boxes 19, and through electric controlling the moving motor 201 by the distribution box 5, the longitudinal electric moving device 10 and the transverse electric moving device 12 are ensured not to slide freely under the situation without manipulation.

The moving motor 201 of the transverse electric moving device 12 is arranged at an outermost end of the trolley connecting plate 9, the moving motor 201 is connected to the speed reducer 202, the speed reducer 202 is fixed at a position of a protruding block at a longitudinal edge of the trolley connecting plate 9, the ball screw 203 is connected to an output end of the speed reducer 202, a length of the ball screw 203 is smaller than or equal to a transverse length of the trolley connecting plate 9, the fixing block 204 sleeves the ball screw 203, and the fixing block 204 is fixed at a bottom of the upper trolley platform 11.

The moving motor 201 of the longitudinal electric moving device 10 is arranged at an outermost end of the upper trolley platform 11, the moving motor 201 is connected to the speed reducer 202, the speed reducer 202 is fixed at a transverse edge of the upper trolley platform 11, the ball screw 203 is connected to an output end of the speed reducer 202, a length of the ball screw 203 is smaller than or equal to a longitudinal length of the upper trolley platform 11, the fixing block 204 sleeves the ball screw 203, and the fixing block 204 is fixed at a bottom of the lifting device support plate 13.

The ball screw 203 adopts a threaded type, and the fixing block 204 adopts a nut type. Under driving of the moving motor 201, the fixing block 204 is immobilized, the ball screw 203 rotates, the transverse electric moving device 12 drives the whole upper trolley platform 11 through the ball screw 203 of the transverse electric moving device 12 to transversely move on the sliding rails 21 through the sliding blocks 22, and the longitudinal electric moving device 10 drives the lifting device support plate 13 through the ball screw 203 of the longitudinal electric moving device 10 to longitudinally move on the guide rails 15 through the sliding blocks 22.

The trolley moving wheels 3 include two universal wheels and two one-way wheels, the universal wheels are mounted at a bottom of the lower trolley platform 2 on a side of the trolley handrail 1, and the one-way wheels are mounted at the bottom of the lower trolley platform 2 away from the side of the trolley handrail 1.

The trolley support legs 4 include electric lifting rods 4*a* and support legs 4*b*, lower ends of the electric lifting rods 4*a* are connected to the support legs 4*b*, and upper ends of the electric lifting rods 4*a* are connected to the lower trolley platform 2. The electric lifting rods 4*a* are electric push rods or hydraulic cylinders; and the support legs 4*b* are made of rubber materials, and are used for enlarging the stress area and increasing frictional force between the trolley and a ground, to prevent sliding or toppling and falling of the trolley during operations and have a certain buffering effect.

The sample box grippers 17 include grappling fixtures 17*a* and stable connecting plates 17*b*, the grappling fixtures 17*a* and the stable connecting plates 17*b* are an integral structure, and clamping blocks 20 being 0.5 cm in height are arranged at front ends of the grappling fixtures 17*a*, whereby the sample boxes are prevented from sliding off accidentally during loading and unloading.

The distribution box 5 is connected to the operation console 6, the electric push rods 14, the moving motor 201 of the transverse electric moving device 12, the moving motor 201 of the longitudinal electric moving device 10, and the electric lifting rods 4*a* of the trolley support legs 4. The distribution box 5 provides electrical energy. Besides, the moving motor 201 of the transverse electric moving device 12, the moving motor 201 of the longitudinal electric moving device 10, the electric push rods 14, and the electric lifting rods 4*a* of the trolley support legs 4 are connected to the operation console 6, whereby starting and stopping are controlled by the operation console 6.

A weight of the upper weight box 16 and a weight of the lower weight box 7 can be adjustable, and can be adjusted according to actual weight calculation of loading and unloading during actual operations.

An embodiment of the trolley during specific test operations is as follows.

In Step 1: the sample box 19 is put on the upper trolley platform 11, the trolley support legs 4 descend, and then the trolley moving wheels 3 are locked; the lifting device support plate 13 is driven to move along the guide rails 15 by the longitudinal electric moving device 10, whereby the sample box grippers 17 upwards reach a position above the sample box 19, the electric push rods 14 are adjusted to enable the sample box grippers 17 to descend, the grappling fixtures 17*a* of the sample box grippers 17 are inserted a clamping slot of the sample box 19, the electric push rods 14 are elevated, the sample box grippers 17 clamp the sample box 19, and at the same time, the sample box 19 is locked with the clamping block 20 on the sample box grippers 17, whereby the sample box 19 is firmly grasped.

In Step 2: the upper trolley platform 11 moves along the sliding rails 21 by the transverse electric moving device 12, the lifting device support plate 13 is driven to move along the guide rails 15 by the longitudinal electric moving device 10, the sample box is above a test equipment, the electric push rods 14 are adjusted to lift and descend, a falling guiding block (191) on the sample box 19 is controlled to fit with the test equipment and then descend, the lifting device support plate 13 retreats back to one end of the upper trolley platform 11 by the longitudinal electric moving device 10, the sample box grippers 17 are withdrawn, and tests are started.

In Step 3: after the Step 1 is repeated to firmly grasp the sample box 19, the electric push rods 14 are adjusted to elevate the sample box 19 to enable the sample box to separate from the test equipment, the lifting device support plate 13 is retreated back to one end of the upper trolley platform 11 by the longitudinal electric moving device 10, the sample box 19 is put on the upper trolley platform 11, and the trolley support legs 4 are withdrawn.

The solution in the embodiment is not intended to limit the scope of patent protection of the present invention. Any equivalent implementation or modification that does not deviate from the present invention is included in the scope of the patent in this case.

What is claimed is:

1. A sample box loading and unloading storage trolley of a rock true-triaxial test instrument, comprising a trolley support framework (8), wherein the trolley support framework (8) is fixed on a lower trolley platform (2), and a lower weight box (7) is arranged in the trolley support framework (8);

wherein trolley moving wheels (3) and trolley support legs (4) are arranged at four corner positions of a bottom of the lower trolley platform (2), a trolley handrail (1) is fixed at a front end of the lower trolley platform (2), and a distribution box (5) and an operation console (6) are arranged on the lower trolley platform (2) between the trolley handrail (1) and the trolley support framework (8);

wherein a trolley connecting plate (9) is arranged above the trolley support framework (8), an upper part of the trolley connecting plate (9) is slidably connected to an upper trolley platform (11) through a transverse electric moving device (12), an upper part of the upper trolley platform (11) is slidably connected to a lifting device support plate (13) through a longitudinal electric moving device (10), electric push rods (14) are fixed at four corners of an upper part of the lifting device support plate (13), an upper weight box (16) is arranged on the lifting device support plate (13), and the upper weight box (16) is located in a space surrounded by the electric push rods (14);

wherein sample box grippers (17) are arranged above the electric push rods (14), and a fixing plate (18) is arranged above the sample box grippers (17); and wherein the fixing plate (18) is detachable for replacing the sample box grippers (17).

2. The sample box loading and unloading storage trolley according to claim 1, wherein sliding rails (21) in a transverse arrangement are symmetrically arranged on an upper surface of the trolley connecting plate (9), two pairs of sliding blocks (22) are symmetrically arranged on the sliding rails (21), the sliding blocks (22) are at a lower end of the upper trolley platform (11), and a length of the sliding rails (21) is the same as a transverse length of the trolley connecting plate (9); and wherein a longitudinal length of the trolley connecting plate (9) is the same as that of the upper trolley platform (11), and the transverse length of the trolley connecting plate (9) is smaller than or equal to that of the upper trolley platform (11).

3. The sample box loading and unloading storage trolley according to claim 1, wherein guide rails (15) in a longitudinal arrangement are symmetrically arranged on an upper surface of the upper trolley platform (11), two pairs of sliding blocks (22) are symmetrically arranged on the guide rails (15), the sliding blocks (22) are at a lower end of the lifting device support plate (13), a transverse width of the upper trolley platform (11) is the same as that of the lifting device support plate (13), and a longitudinal length of the upper trolley platform (11) is larger than that of the lifting device support plate (13).

4. The sample box loading and unloading storage trolley according to claim 1, wherein the transverse electric moving device (12) and the longitudinal electric moving device (10) have a same structure, and each comprise a moving motor (201), a speed reducer (202), a ball screw (203) and a fixing block (204);

wherein the moving motor (201) of the transverse electric moving device (12) is arranged at an outermost end of the trolley connecting plate (9), the moving motor (201) is connected to the speed reducer (202), the speed reducer (202) is fixed at a position of a protruding block at a longitudinal edge of the trolley connecting plate (9), the ball screw (203) is connected to an output end of the speed reducer (202), a length of the ball screw (203) is smaller than or equal to a transverse length of the trolley connecting plate (9), the fixing block (204) sleeves the ball screw (203), and the fixing block (204) is fixed at a bottom of the upper trolley platform (11); and wherein the moving motor (201) of the longitudinal electric moving device (10) is arranged at an outermost end of the upper trolley platform (11), the moving motor (201) is connected to the speed reducer (202), the speed reducer (202) is fixed at a transverse edge of the upper trolley platform (11), the ball screw (203) is connected to an output end of the speed reducer (202), a length of the ball screw (203) is smaller than or equal to a longitudinal length of the upper trolley platform (11), the fixing block (204) sleeves the ball screw (203), and the fixing block (204) is fixed at a bottom of the lifting device support plate (13).

5. The sample box loading and unloading storage trolley according to claim 1, wherein the trolley moving wheels (3) comprise two universal wheels and two one-way wheels, the universal wheels are mounted at a bottom of the lower trolley platform (2) on a side of the trolley handrail (1), and the one-way wheels are mounted at the bottom of the lower trolley platform (2) away from the side of the trolley handrail (1).

6. The sample box loading and unloading storage trolley according to claim 1, wherein the trolley support legs (4) comprise electric lifting rods (4*a*) and support legs (4*b*), lower ends of the electric lifting rods (4*a*) are connected to the support legs (4*b*), and upper ends of the electric lifting rods (4*a*) are connected to the lower trolley platform (2).

7. The sample box loading and unloading storage trolley according to claim 1, wherein the sample box grippers (17) comprise grappling fixtures (17*a*) and stable connecting plates (17*b*), the grappling fixtures (17*a*) and the stable connecting plates (17*b*) are an integral structure, and clamping blocks (20) being 0.5 cm in height are arranged at front ends of the grappling fixtures (17*a*).

* * * * *